(12) United States Patent
Welker et al.

(10) Patent No.: US 8,347,694 B2
(45) Date of Patent: Jan. 8, 2013

(54) LNG COLLECTION SYSTEM AND METHOD

(75) Inventors: Brian H. Welker, Fulshear, TX (US);
Tracy Dean Peebles, Houston, TX (US);
Dennis M. McKay, Richmond, TX (US); Margie McKay, legal representative, Richmond, TX (US);
Thomas S. Green, Richmond, TX (US)

(73) Assignee: Welker, Inc., Sugar Land, TX (US)

( * ) Notice: Subject to any disclaimer, the term of this patent is extended or adjusted under 35 U.S.C. 154(b) by 440 days.

(21) Appl. No.: 12/173,800

(22) Filed: Jul. 15, 2008

(65) Prior Publication Data

US 2010/0012201 A1 Jan. 21, 2010

(51) Int. Cl.
*G01N 1/00* (2006.01)

(52) U.S. Cl. ...................................... 73/64.56
(58) Field of Classification Search ................ 73/863.11
See application file for complete search history.

(56) References Cited

U.S. PATENT DOCUMENTS

| | | | | |
|---|---|---|---|---|
| 2,665,239 A | * | 1/1954 | Howard et al. | 29/37 R |
| 3,972,202 A | * | 8/1976 | Stearns | 62/50.1 |
| 4,066,892 A | * | 1/1978 | Givens | 376/165 |

OTHER PUBLICATIONS

Refrigerated Light Hydrocarbon fluids—Sampling of Liquefied Natural Gas—Continuous and Intermittent Methods, International Standard 8943, Second Edition, Mar. 1, 2007.
Manual of Petroleum Measurement Standards, Chapter 17—Marine Measurement, Section 10—Measurement of Refrigerated and/or Pressurized Cargoes on Board Gas Carriers and Barges, May 5, 2005.
Obtaining Natural Gas Samples for Analysis by Gas Chromatography, Gas Processors Association, GPA Standard 2166-05, Revised 2005, Tulsa, Oklahoma, www.gasprocessors.com.
Manual of Petroleum Measurement Standards, Chapter 14—Natural Gas Fluids Measurement, Section 1—Collecting and Handling of Natural Gas Samples for Custody Transfer, Sixth Edition, Feb. 2006.

* cited by examiner

*Primary Examiner* — Peter Macchiarolo
*Assistant Examiner* — Alex Devito
(74) *Attorney, Agent, or Firm* — Husch Blackwell LLP

(57) ABSTRACT

An LNG sampling system is provided which includes a sampling probe. The sampling probe includes a backflow prevention check valve positioned within the probe adjacent the inlet end. The probe is inserted into a source of LNG to extract samples of LNG by providing a pressure differential between the probe piping system and the pressure of the LNG within the source. In the event the pressure in the piping system increases above a predetermined amount, the check valve will close preventing backflow of LNG from the sampling system back into the source.

10 Claims, 3 Drawing Sheets

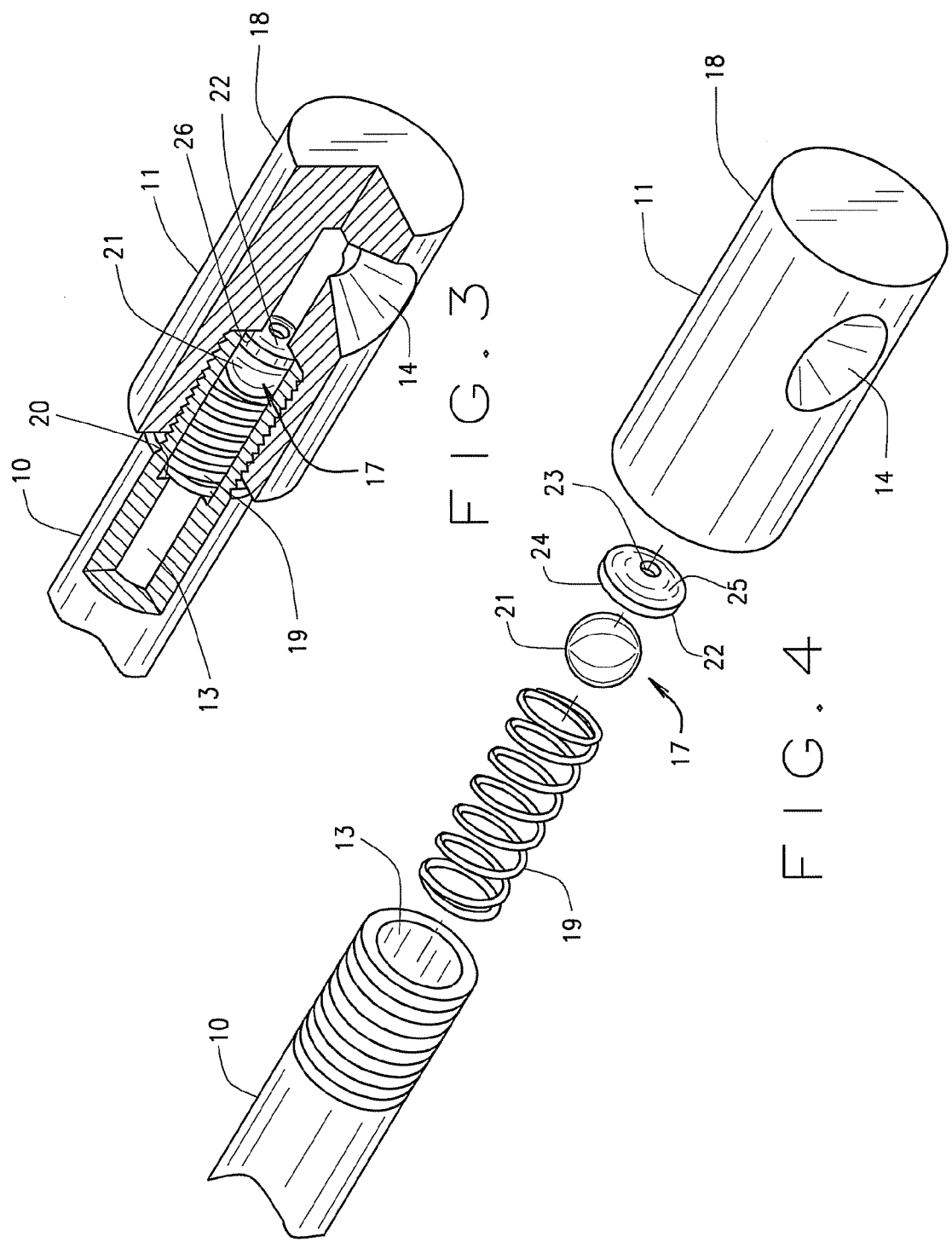

LNG COLLECTION SYSTEM AND METHOD

BACKGROUND OF INVENTION

The collection of LNG for analysis is well known. There are standards established for how to sample LNG to provide a representative sample for analysis. Analysis is typically performed in order to establish the BTU value of the LNG to properly price the product. LNG is not a pure compound, but a mixture of various components with each component having a potentially different BTU value. There may also be impurities such as moisture, nitrogen and other components that can affect the BTU value of the LNG. The LNG may be sampled either in a somewhat continuous manner by extracting samples from, for example, a pipeline or loading arm and conveying the samples to the analytical equipment through a piping system. Such a system is often used at a ship offloading site. Another method is to take samples in a "batch" manner using sampling cylinders. Both processes are well known in the art and can be found for example in ISO 8943 or API 17.10 for LNG or API 14.1 and GPA 2166 for typical natural gas. While sampling of natural gas in its gaseous state is relatively straight forward, sampling liquified natural gas (LNG) poses special problems.

Natural gas can be liquified by changing its pressure and/or temperature. At atmospheric pressure, natural gas is a liquid at about −250° F. or colder. At 4000-5000 psi, natural gas can be maintained as a liquid, at ambient temperatures. If the temperature is elevated or pressure is reduced, one or more components of the LNG can vaporize skewing the distribution of the various compounds making up the natural gas in the sample thereby adversely affecting the analysis and its validity in indicating the BTU value of the gas. In an onsite monitoring system where the analytical equipment is connected to the source of LNG, the vaporization of the LNG is intentionally effected at some point prior to the sample reaching the analytical equipment, for example a gas chromatograph. In the process of continuous sampling, i.e., the taking of samples from a source and conveying through a piping system to an analyzer, a probe or other device is inserted into the source, for example, a pipeline or tank. The probe has an open end that exposes the flow path and the piping system to flow communication of LNG from the source. Thus, if the conditions in the piping system are such as to allow the LNG to vaporize, backflow in the piping system can occur and affect the representative nature of the sample within the sampling piping system. If LNG vaporizes, its volumetric expansion from liquid to gas is on the order of 600 fold resulting in an increase in pressure and temperature. This expansion can cause backflow of product in the sampling lines. This then can lead to the providing of a non-representative sample to the analyzer for analysis. Lighter components will take the course of least resistance and can provide for a disproportionate representation of heavier components to enter the analyzer.

It would thus be desirable to provide a continuous sampling system and method that reduces the risk of providing non-representative samples for analysis.

SUMMARY OF INVENTION

The present invention involves the provision of an LNG sampling system usable for continuous sampling or spot sampling. The system involves a probe for insertion into a source of LNG. The probe has an inlet at a distal end portion and an outlet at a proximal end portion. The tube portion of the probe is mounted to a mounting member adjacent the proximal end portion and is adapted to fix the tube to a device, such as a pipeline, containing LNG. A pressure responsive check valve is associated with the tube flow wise between a sampler (analyzer) and the LNG source and is operable to selectively prevent flow in a direction from the tube to the source if pressure in the tube exceeds the pressure of LNG in the source at a pressure differential greater than about 2 psi.

The present invention also involves the provision of a method of extracting a representative LNG sample from a source of LNG. The method includes positioning a sampling probe in flow communication with a source of LNG. LNG is extracted through a tube portion of the probe. The probe is connected to a piping system to allow the extracted LNG to flow from the probe tube to an LNG analyzer. The piping system is exposed to an environment where the temperature of the extracted LNG can result in vaporization of at least a portion of the extracted LNG. Escape of any appreciable portion of vaporized or downstream liquid LNG is prevented with a check valve associated with the sampling probe tube.

The present invention also involves the provision of an LNG sampling probe. The probe includes an elongate tube having a distal end portion and a proximal end portion with an inlet adjacent the distal end portion and an outlet adjacent the proximal end portions. A mounting member is associated with the tube and is positioned adjacent the proximal end adapted to fix the conduit to a device containing LNG. A pressure responsive check valve is associated with the tube adjacent the distal end portion and is operable to prevent flow from the conduit and out the inlet. The check valve has an opening setting in the range of between about 5 psi and about 15 psi pressure differential. The tube has a transverse cross-sectional area of less than about 0.025 in$^2$ and preferably less than about 0.01 in$^2$.

DETAILED DESCRIPTION OF DRAWINGS

FIG. 3 is an enlarged isometric view of a distal end portion of the sampling probe with portions broken away to show details therein.

FIG. 4 is an exploded isometric view of the sampling probe as seen in FIG. 3.

Like numbers throughout the various Figures designate like or similar parts and/or construction.

DETAILED DESCRIPTION

Figure 1:
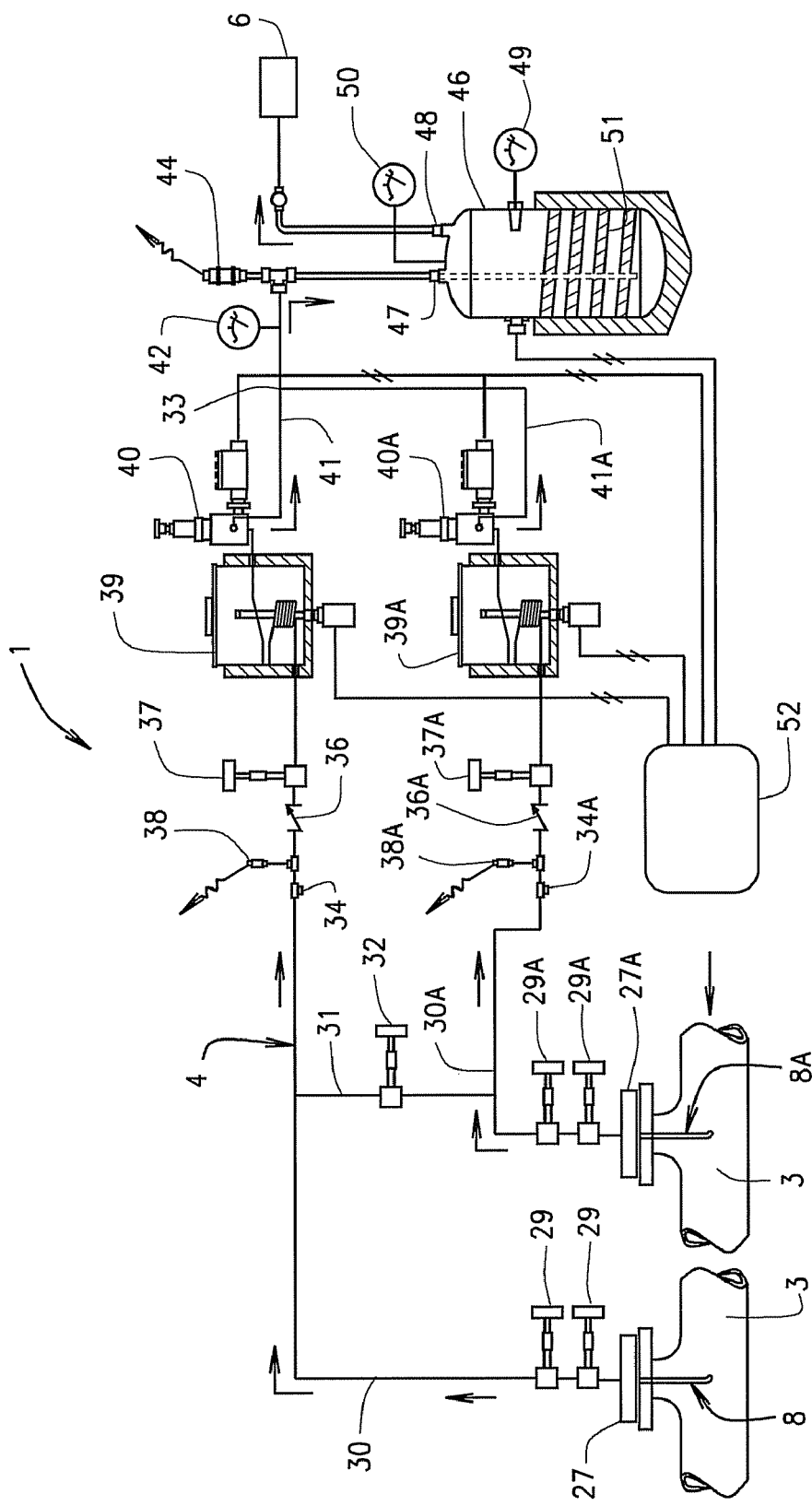
FIG. 1 is a schematic illustration of an LNG sampling system adapted for continuous sampling.

The reference numeral 1 designates generally an LNG sampling system operable to extract LNG (liquified natural gas) from a source 3, conveying LNG through a piping system designated generally 4 to an analyzer designated generally 6 operable to provide an analysis of an LNG sample. The operation is continuous, i.e., able to substantially continuously extract samples of LNG recognizing that there may not be fully continuous sample extractions since samples are analyzed in batch quantities. The analyzer 6 can be used to calculate or provide the BTU value of an LNG sample. The analyzer 6 can be, for example, a gas chromatograph or a calorimeter. The extracted sample from the source 3 can include LNG with a distribution range of various components and other materials such as oxygen, nitrogen, etc. The source 3 may be a pipeline through which the LNG flows or the LNG can be sampled from a container through a loading arm, such as a tank or a ship storage compartment from which the LNG flows. The system 1 includes at least one sampling probe designated generally 8 and is positioned at a desired location in the source 3 for the extraction of samples of LNG therethrough. The position of probe 8 within the source 3 is well known in the art.

Figure 2:
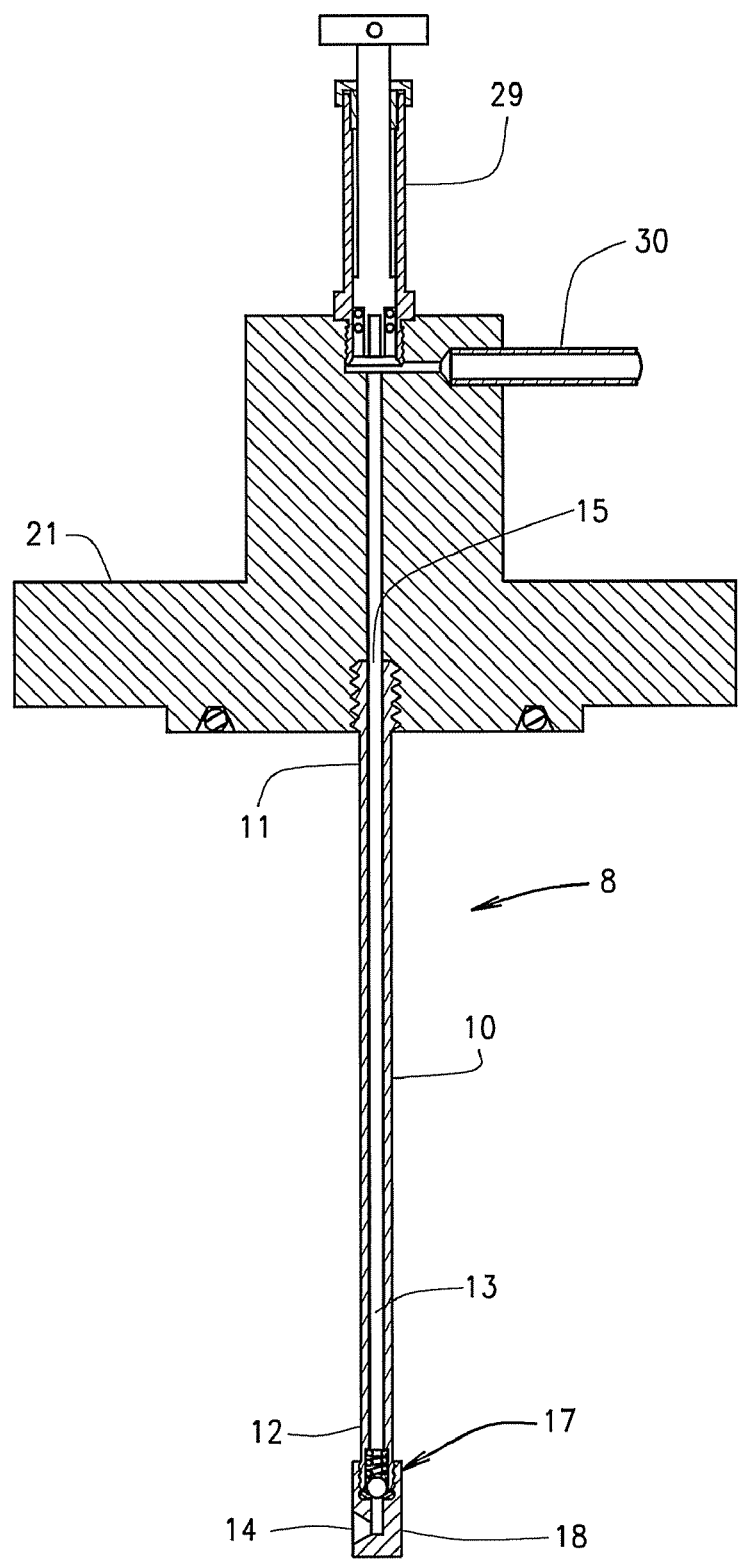
FIG. 2 is a transverse sectional view of the sampling probe used in the system shown in FIG. 1.

The probe 8, as best seen in FIGS. 2-4, includes a conduit or tube 10 having a proximal end portion 11 and a distal end portion 12. The tube 10 has a flow path 13 extending between the end portions 11, 12 and provides for flow communication between an inlet 14 and an outlet 15. Inlet and outlet and other flow terms used herein are used to designate flow or construction for flow in a normal direction of operation of the system 1, i.e., from the pipeline or source 3 to the analyzer 6. The probe 8 is provided with a check valve arrangement 17 that will allow out flow of fluid from the source 3 through the inlet 14 along the flow path 13 to the outlet 15. The check valve 17 will open at a pressure differential in the range of between about 5 psi and about 15 psi. As shown, the check valve 17 is located in a removable inlet tip 18. The tip 18 is mounted on the tube 10 at the distal end portion 12 as by threaded engagement. The inlet 14 is located in the tip 18 and is preferably configured to be directed in a direction generally normal to the longitudinal axis of the tube 10 when used in a source 3 having flowing LNG and opens generally upstream. The inlet 14 can be generally cone-shaped tapering from a larger open end toward a smaller outlet end opening into the flow path 13. In the illustrated embodiment, the check valve 17 includes a biasing spring 19 which has one end seated against a shoulder 20 and another end engaging a moveable valve element 21 which is shown as being in the form of a spherical ball. The spring 19 provides a biasing force on the valve element 21 to seat it against a valve seat 22 by biasing the check valve 17 to a closed or no flow condition until a predetermined pressure differential is achieved, i.e., the pressure at the source 3 exceeds the pressure at the outlet 15. Preferably, the valve seat 22 is a separate element and can be removed from the tip 18 for replacement or maintenance. Preferably, the valve seat 22 is made of a synthetic or polymeric material such as PTFE, PEEK, Delrin, Florosint, etc. A suitable seat is available from SKF Polyseal, Inc. Salt Lake City, Utah and is denoted as part number BUC-180-00.125-069. As shown, the valve seat member 22 is in the form of an annular ring having two generally opposed planar surfaces 24, 25 with a centrally located through opening 23. The valve element 21 seats against a surface 24. The opening 23 extends between the surfaces 24 and 25. The valve seat member 22 rests against a shoulder 26 in the tip 18. When closed, the valve element 21 will extend into the opening 23 and engage an edge portion defining an outlet side of the opening 23. The probe 8 includes and defines the sample flow path 13 along its length. Preferably, the flow path has a transverse cross sectional area of less than about 0.025 in$^2$ and preferably less than about 0.01 in$^2$.

A mounting device 27 has the probe 18 suitably mounted thereto. The illustrated mounting is by threaded inter-engagement to facilitate repair and/or construction. The mount 27 is adapted for mounting the probe 8 to the source 3 in a sealed manner. Because the fluid contained in the source 3 is liquid, it would typically, at normal operating pressures, for example 40 psi gage, be at a temperature of approximately −256° F. Thus, the materials from which the probe 8, mount 27 and any seals provided for between the mount 27 and source 3 should be adapted for long life at this operating temperature.

In the illustrated structure, one or more valves 29 are provided to provide shutoff of flow between a probe 8 and the piping system 4. As shown in FIG. 2, two valves 29 are provided and can be provided in the piping system 4, as part of the mount 27, or in both places to provide redundant valving for safety purposes. The piping system 4 includes a conduit 30. As seen in FIG. 1, there are redundant feed streams to the analyzer 6 with each of the separate feed streams being shown as substantially identical. For the purposes of description, the second feed stream will be denoted with an A following the part number, for example, the conduit 30 in one feed stream will be the conduit 30A in the second feed stream. As seen, the conduits 30, 30A can be connected together in selective flow communication for example with a conduit 31 having an isolator valve 32 therein to either join the two feed streams in flow communication or to preclude flow communication therebetween. The feed streams are also connected together at a downstream portion as at 33. The conduit 30 includes a particle filter 34 upstream of other equipment in the piping system 4. A check valve 36 such as a Welker Cryogenic Check Valve is provided downstream of the filter 34 to prevent backflow of fluid within the conduit 30 downstream of the valve 36. There is preferably provided an on/off valve 37 for manually or remote activation to permit or preclude flow of fluid through the conduit 30. A pressure relief valve 38 may also be provided set to protect the piping system 4 and/or downstream equipment. As seen, downstream of the valve 37 is a vaporizer unit 39. Fluid from the source 3 flows into the vaporizer 39 and is heated to a temperature adequate to vaporize the LNG. Preferably, the LNG is heated to a temperature in the range of between about 10° F. and about 60° F. Connected to the downstream or outlet side of the vaporizer 39 there is provided a pressure regulator 40 such as a Welker Convection by Conduction heated regulator that will control the outfeed pressure to the conduit 41. The fluid in the conduit 41 is preferably at least a significant portion vapor. Pressure and/or temperature gages 42 can be provided in the conduit 41 or sensors to provide remote readout of conditions. There can be provided in the conduit 41/41A, after they join at 33, a pressure relief valve 44. The pressure relief valve 44 (as well as the valves 38, 38A) can vent to a collection system to prevent bleeding of excess LNG to the atmosphere. Such collection systems are well known in the art. The conduit 41 connects the vaporizer 39 flow wise to an accumulator 46. The conduit 41 and conduit 41A are connected in flow communication to an inlet 47 of the accumulator 46. An outlet 48 of the accumulator 46 is provided that connects the accumulator 46 to the analyzer 6 such as a gas chromatograph or calorimeter. Temperature and pressure gages 49, 50, respectively, are provided to provide temperature and pressure readings for the contents of the accumulator 46. Vaporized, or at least partially vaporized, LNG and other components of the feed stream(s) are fed to the accumulator 46 for further heating. Preferably, the LNG is heated to a temperature on the order of about 90° F. or other suitable temperature above the freezing point of water for processing of samples in the analyzer 6. The accumulator 46 can be provided with a suitable heater 51 such as an electrically resistant heat tracing. A suitable accumulator 46 for most LNG sampling systems can be on the order of about three liters (3,000 cc's). Heat may be supplied to the vaporizer 39 and accumulator 46 via a power supply 52 as well as to other electrically operated equipment such as the heated regulators 40, 40A.

In the event the LNG vaporizes in the conduit 30, its pressure will increase to a pressure above the pressure in the pipeline or source 3 potentially causing backflow of LNG. This can disrupt the integrity of the samples being taken. In the event there is vaporization, an increase in pressure will cause the check valve 17 to close preventing backflow out of the piping system 4.

The present invention is better understood by a description of the operation thereof. LNG is provided substantially continuously from a source 3 such as a pipeline, for example, at an offloading facility for LNG tanker ships. The source 3 may also be any other suitable source of LNG. Typically, the source 3 will have the LNG flowing. The sampling tube 10 portion of the probe 8 is positioned in the source 3 to permit flow of LNG from the source through the conduit 31 and/or 31A. LNG is extracted through the tube 10 and fed to the conduit 30 and/or conduit 30A of the piping system 4. The LNG is then exposed, in the conduit 30, 30A to an environment that could possibly permit its vaporization if the pressure is reduced and/or the temperature of the LNG is allowed to increase, for example, during a flow static period or a time that there is cessation of flow through the piping system 4. In the event of vaporization, the pressure in the conduit 30, 30A will increase sufficiently and as predetermined, the valve 17 moves to a closed position wherein the valve element 21 engages the valve seat 22, both under the influence of the spring 19 and the increased line pressure. Thus, the integrity of the samples being taken is maintained.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A method of measuring the BTU content of an LNG sample from a source of LNG to prevent backflow of portions of the sample through a probe and back into the source which disrupts the integrity of the LNG sample, said method comprising:
   positioning at least a portion of a probe in a source of LNG, where LNG in said source is stored at about −250° F., said probe defining a sample flow path for the LNG;
   extracting an LNG sample through a pressure responsive check valve in the sample flow path of the probe, said pressure responsive check valve having a valve seal in the form of an annular ring having two generally opposing planar surfaces with a centrally located aperture that further defines the sample flow path;
   passing the LNG sample from the probe through a piping system and a second check valve to a vaporizer unit where the LNG sample is warmed and changed from a liquid phase to a gas phase natural gas sample, the second check valve preventing reverse flow of the gas phase natural gas sample from the vaporizer unit into said piping system;
   passing the gas phase natural gas sample through an accumulator and warming the gas phase natural gas sample to a temperature above 32° F.;
   passing the gas phase natural gas sample into an analyzer where the BTU content of the gas phase natural gas sample is determined; and
   preventing backflow of any components from said piping system back to the LNG source in the event of an unwanted vaporization of at least a portion of the LNG sample in said piping system by selective closing of the pressure responsive check valve, which exposes one of the two generally opposing planar surfaces of the valve seal to liquid phase LNG and the opposing planar surface to the gas phase of the components during an unwanted vaporization of at least a portion of the LNG sample in said piping system.

2. The method as set forth in claim 1 wherein the pressure responsive check valve further includes a movable valve element which is generally spherical in shape and sized and arranged to engage the valve seal to close the centrally located aperture and prevent back flow of the components through the pressure responsive check valve.

3. The method of claim 2 wherein the pressure responsive check valve opening at a pressure differential in the range of between about 5 psi and about 15 psi.

4. The method as set forth in claim 3 wherein the LNG sample is heated to a temperature above the freezing point of water prior to analysis.

5. An LNG sampling system to prevent backflow of portions of the LNG sample through a probe and back into the source which disrupts the integrity of an LNG sample, the system comprising:
   a probe in fluid communication with a source of LNG having at least a portion of the probe positioned in the source of LNG, where LNG in said source is stored at about −250° F.;
   a pressure responsive check valve in a sample flow path of the probe, said pressure responsive check valve having a valve seal in the form of an annular ring having two generally opposing surfaces with a centrally located aperture that further defines the sample flow path from the LNG source through the probe;
   a piping system in fluid communication with the probe and the piping system further defining a sample flow path for the LNG sample;
   a vaporizer unit in fluid communication with the piping system to convert the liquid phase LNG sample to a gas phase natural gas sample;
   an accumulator in fluid communication with the vaporizer, the accumulator including a heater to warm the gas phase natural gas sample to a temperature above the freezing point of water;
   an analyzer in fluid communication with the accumulator to analyze the BTU content of the gas phase natural gas sample;
   at least a portion of said piping system being exposed to a temperature above a vaporization point of the components in an extracted LNG sample; and
   said pressure responsive check valve positioned in a tip of the probe operable to selectively close with a bubble tight seal to prevent backflow of the components from said piping system to the source if pressure in said piping system exceeds pressure of the LNG in the source.

6. The sampling system of claim 5 wherein the pressure responsive check valve further includes a movable valve element being generally spherical in shape and sized and arranged to engage the valve seal in the form of the annual ring having two generally opposing planer surfaces to selectively seal against the centrally located aperture to prevent backflow of the components from said piping system into the source of LNG.

7. The sampling system of claim 6 wherein the tube having a sample flow path with a transverse cross sectional area of less than about 0.025 in$^2$.

8. An aftermarket kit to attach to an existing LNG sampling system to prevent backflow of portions of and LNG sample from a piping system through a probe and back into the source which disrupts the integrity of the LNG sample comprising:
- a probe with an elongate conduit having a distal end and a proximal end with an inlet adjacent the distal end, said conduit having a sample flow path along at least a portion of its length with a transverse cross sectional area of less than about 0.025 in$^2$;
- a mounting member associated with the probe and adjacent the proximal end adapted to fix at least a portion of the probe in to a device containing a source of LNG stored at about −250° F.; and
- a pressure responsive check valve positioned in the probe adjacent the distal end and operable to prevent backflow of the components in the LNG sample from a piping system through the probe into the source of LNG, the pressure responsive check valve having a resilient member to provide a biasing force on a generally spherical valve element to seat the generally spherical valve element against a valve seat in the form of an annular ring having two generally opposing surfaces with a centrally located aperture by biasing the pressure responsive check valve to close until a predetermined pressure differential is achieved between the pressure in the source of LNG and the pressure in the proximal end of the probe.

9. The aftermarket kit of claim 8 further including a second valve for mounting upstream of and proximate to the vaporizer unit.

10. The sampling system of claim 7 further including a second check valve for mounting upstream of and proximate to the vaporizer unit.

* * * * *

UNITED STATES PATENT AND TRADEMARK OFFICE
CERTIFICATE OF CORRECTION

PATENT NO. : 8,347,694 B2
APPLICATION NO. : 12/173800
DATED : January 8, 2013
INVENTOR(S) : Brian H. Welker Page 1 of 1

It is certified that error appears in the above-identified patent and that said Letters Patent is hereby corrected as shown below:

In the Claims:

Claim 8, Col. 7, line 5, delete "and LNG" and replace with -- an LNG --

Claim 8, Col. 7, line 15, delete "in to" and replace with -- in --

Signed and Sealed this
Twenty-third Day of April, 2013

Teresa Stanek Rea
*Acting Director of the United States Patent and Trademark Office*